(12) United States Patent
Xing (10) Patent No.: US 8,980,554 B2
(45) Date of Patent: Mar. 17, 2015

(54) GENETIC MAKE-UP MODIFIES CANCER OUTCOME

(75) Inventor: Michael Mingzhao Xing, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/812,581

(22) PCT Filed: Jul. 26, 2011

(86) PCT No.: PCT/US2011/045340
§ 371 (c)(1),
(2), (4) Date: Jan. 28, 2013

(87) PCT Pub. No.: WO2012/018613
PCT Pub. Date: Feb. 9, 2012

(65) Prior Publication Data
US 2013/0171645 A1    Jul. 4, 2013

Related U.S. Application Data (60) Provisional application No. 61/367,684, filed on Jul. 26, 2010, provisional application No. 61/432,780, filed on Jan. 14, 2011.

(51) Int. Cl.
*C12Q 1/68* (2006.01)
*C12P 19/34* (2006.01)
*C12N 9/64* (2006.01)
*C07H 21/02* (2006.01)
*C07H 21/04* (2006.01)

(52) U.S. Cl.
CPC ............ *C12Q 1/6886* (2013.01); *C12N 9/6491* (2013.01)
USPC .......... 435/6.1; 435/91.2; 536/23.1; 536/24.3

(58) Field of Classification Search
None
See application file for complete search history.

(56) References Cited

PUBLICATIONS

G Tallini, M Santoro, M Helie, et al. Clin Cancer Res 1998;4:287-294.*
Pennisi E. Science (Sep. 18, 1998) 281;5384, p. 1787-1789.*
Juppner, H. Bone vol. 17, No. 2, Supplement, Aug. 1995:39S-42S.*
Hegele, R.A. Arterioscler Thromb Vasc Biol. 2002;22:1058-1061.*
Gonzalez-Arriaga, P., et al., BMC Cancer, vol. 8:378, Dec. 2008.
Nan, H., et al., Cancer Epidemiol Biomarkers Prev., vol. 17, pp. 3551-3557, Dec. 2008.
Decock, J., et al., Cancer Research, vol. 67, pp. 10214-10221, Nov. 2007.
Wang, H., et al., Human Molecular Genetics, vol. 13, No. 21, pp. 2659-2669, Sep. 2004.

* cited by examiner

*Primary Examiner* — Stephen Kapushoc
(74) *Attorney, Agent, or Firm* — Johns Hopkins Technology Transfer (57) ABSTRACT

A frequent SNP A259G (K87E) genotype switch in the MMP8 gene in has been found to modify the clinical behavior of cancers. The modification varies based on the patient's genotype for the SNP, and whether homozygous or heterozygous. One particular genotype for this SNP leads to more aggressive tumor behavior and worst clinical outcome than the others.

1 Claim, 2 Drawing Sheets

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: amplification primer

<400> SEQUENCE: 1
tggaggccag tgttgtagga c                                             21

<210> SEQ ID NO 2
<211> LENGTH: 21
```

```
<212> TYPE: DNA
<213> ORGANISM: Artificial Sequence
<220> FEATURE:
<223> OTHER INFORMATION: amplification primer

<400> SEQUENCE: 2
atagcctaag atatctgaca c                                              21

<210> SEQ ID NO 3
<211> LENGTH: 21
<212> TYPE: DNA
<213> ORGANISM: Artificial Sequence
<220> FEATURE:
<223> OTHER INFORMATION: amplification primer

<400> SEQUENCE: 3
agcgactcag cattgtagac t                                              21

<210> SEQ ID NO 4
<211> LENGTH: 21
<212> TYPE: DNA
<213> ORGANISM: Artificial Sequence
<220> FEATURE:
<223> OTHER INFORMATION: amplification primer

<400> SEQUENCE: 4
tcactgtgga atttgatctt g                                              21

<210> SEQ ID NO 5
<211> LENGTH: 21
<212> TYPE: DNA
<213> ORGANISM: Artificial Sequence
<220> FEATURE:
<223> OTHER INFORMATION: amplification primer

<400> SEQUENCE: 5
aaactgctgg gaaaccatag t                                              21

<210> SEQ ID NO 6
<211> LENGTH: 21
<212> TYPE: DNA
<213> ORGANISM: Artificial Sequence
<220> FEATURE:
<223> OTHER INFORMATION: amplification primer

<400> SEQUENCE: 6
taactcatcc tgaattgtag c                                              21

<210> SEQ ID NO 7
<211> LENGTH: 21
<212> TYPE: DNA
<213> ORGANISM: Artificial Sequence
<220> FEATURE:
<223> OTHER INFORMATION: amplification primer

<400> SEQUENCE: 7
aagacagcaa ggcaggctga t                                              21

<210> SEQ ID NO 8
<211> LENGTH: 21
<212> TYPE: DNA
<213> ORGANISM: Artificial Sequence
<220> FEATURE:
<223> OTHER INFORMATION: amplification primer

<400> SEQUENCE: 8
```

```
ctatgtcaaa tctttgcccc c                                              21

<210> SEQ ID NO 9
<211> LENGTH: 21
<212> TYPE: DNA
<213> ORGANISM: Artificial Sequence
<220> FEATURE:
<223> OTHER INFORMATION: amplification primer

<400> SEQUENCE: 9
tgagactgca caataatgct t                                              21

<210> SEQ ID NO 10
<211> LENGTH: 21
<212> TYPE: DNA
<213> ORGANISM: Artificial Sequence
<220> FEATURE:
<223> OTHER INFORMATION: amplification primer

<400> SEQUENCE: 10
ctcaattcac agatcagact g                                              21
```

GENETIC MAKE-UP MODIFIES CANCER OUTCOME

This invention was made using funds from the U.S. government. The U.S. retains certain rights in the invention under the terms of National Institutes of Health grant CM34225.

CROSS-REFERENCE TO RELATED APPLICATIONS

This application is a 35 U.S.C. 371 U.S. national entry of International Application PCT/US2011/045340 having an international filing date of Jul. 26, 2011, which claims the benefit of U.S. Provisional Application No. 61/367,684 filed Jul. 26, 2010 and U.S. Provisional Application No. 61/432,780 filed Jan. 14, 2011, the content of each of the aforementioned applications are herein incorporated by reference in their entireties.

TECHNICAL FIELD OF THE INVENTION

This invention is related to the area of cancer. In particular, it relates to genetic factors that modify outcome.

BACKGROUND OF THE INVENTION

Follicular epithelial cell-derived thyroid cancer is the most common endocrine malignancy with a high incidence worldwide (1, 2). This cancer is histologically classified into papillary thyroid cancer (PTC), follicular thyroid cancer (FTC), and anaplastic thyroid cancer (ATC) (3). Thyroid cancers frequently harbor activating mutations in the MAP kinase (MAPK) and phosphatidylinositol 3-kinases (PI3K)/Akt signaling pathways (4), as represented by RAS, BRAE, and RET/PTC mutations in the former and PIK3C4 and PTEN mutations in the latter. As an important mechanism for the tumorigenesis of thyroid cancer and many other human cancers, aberrant activation of the two signaling pathways by such mutations can cause uncontrolled cell division, proliferation and survival.

Somatic mutations of GNAQ, MMP8, Akt3, EGER and PIK3R1 genes have been recently reported in some human cancers with various prevalences and they can activate the MAPK and PI3K/Akt signaling pathways (5-10). A particularly frequent somatic mutation of the GNAQ gene at codon 209, resulting in mutant GNAQ$^{Q209L}$, has been reported in uveal melanoma and blue nevi (5). The GNAQ gene encodes a G-protein α subunit that mediates signals from G-protein-coupled receptors (GPCRs) to the MAPK pathway. The normal amino acid, glutamine, encoded by codon 209 of the GNAQ gene ties within the RAS-like domain of GNAQ (corresponding to residue 61 of Ras) and is essential for GTP hydrolysis. Recent studies found no mutation in GNAQ in PTC, MTC and FTC, but it has not been analyzed in the more aggressive type of thyroid cancer, ATC (11-13). Matrix metalloproteinases (MMPs) are proteolytic enzymes that degrade components of extra cellular matrix and basement membranes. Abnormalities of MMPs have been associated with cancer metastasis. Frequent mutations of the MMP8 gene have been observed in melanoma (6). Most of the mutations in this gene have been observed in exon 2. All the mutants detected in this exon, including S50F, P78S, K87N and G104R, were shown to be tumorigenic and the wild-type has been shown to inhibit cell growth on soft agar and tumor formation in vivo (6). A point mutation in the pleckstrin homology domain (E17K) and a point mutation in the regulatory C-terminal domain (E438D) of AKT3 were recently found in melanomas (7, 8). Expression of the AKT3 E17K in A375 cells has been demonstrated to increase AKT phosphorylation as compared with the wild-type AKT3 (7). A recent study reported an AKT3 mutation in PTC, but FTC and ATC were not examined in this study (14). Varying frequencies of EGER mutation in PTC had been reported in two studies (9, 15). The status of somatic EGER mutation is not known in this cancer in the American patients, while other types of cancers such as FTC and ATC have been reported (4). The class IA PI3K lipid kinase has a catalytic subunit (p110α) and a regulatory subunit (p85α), which is encoded by PIK3CA and PIK3R1 genes, respectively. Somatic mutations of PIK3G1 gene are common in human cancers. Recently, mutations have also been found in the PIK3R1 gene in human cancers (10). These mutations in PIK3R1 are all shown to promote cell survival, anchorage-independent cell growth and tumorigenesis through AKT activation in a p110-dependent manner (10). The mutation status in the GNAQ, MMP8, AKT3, EGFR and PIK3R1 genes had been incompletely examined or not examined in thyroid cancers.

There is a continuing need in the art to develop a fuller understanding of the genetic factors that affect human cancers so that they can be better identified, treated, and managed.

SUMMARY OF THE INVENTION

According to one aspect of the invention a method is provided to stratify a patient having a cancer based on a genotype affecting clinical outcome. A test sample of the patient is tested and a biallelic, germline genotype of the patient for matrix metalloproteinase 8 (MMP8) gene at nucleotide position 259 of its transcribed sequence is determined. An AA genotype is associated with a poor clinical outcome. A GG genotype is associated with an intermediate clinical outcome. An AG genotype is associated with a better clinical outcome. These genotypes refer to the coding strand of genomic nucleic acid.

According to another aspect of the invention a method is provided to stratify a patient having a benign tumor or pre-cancerous lesion based on a genotype affecting clinical outcome. A test sample of the patient is tested and a biallelic, germline genotype of the patient for matrix metalloproteinase 8 (MMP8) gene at nucleotide position 259 of its transcribed sequence is determined. An AA genotype is associated with higher risk of becoming malignant. A GG genotype is associated with an intermediate risk of becoming malignant. An AG genotype is associated with a lower a higher risk of becoming malignant. These genotypes refer to the coding strand of genomic nucleic acid.

These and other embodiments which will be apparent to those of skill in the art upon reading the specification provide the art with methods of categorizing, assessing, predicting, and testing patients with precancerous lesions, benign tumors, or cancers.

BRIEF DESCRIPTION OF THE DRAWINGS

FIG. 1A-1D. Detection of MMP8 and EGFR mutations. (FIG. 1C) Schematic diagram of EGFR showing a mutation (G735S) and a single nucleotide polymorphism (K757K)

identified in thyroid cancer. The EGFR gene is located on chromosome 7p11.2 contains 28 exons and interveining sequences.

DETAILED DESCRIPTION OF THE INVENTION

Although we found no mutation in the MMP8 gene, we found a common A259G SNP (rs1940475), resulting in a K87E amino acid switch in the proteoglycan binding domain of MMP8. The more common nucleotide pattern is G259, resulting in amino acid glutamic acid at position 87 of MMP8 and seen in about 70-90% of thyroid cancer cases. The less common nucleotide pattern is A259, resulting in amino acid lysine at position 87 and conversely seen in about 10-30% of the cases of thyroid cancer. We further investigated the biological and pathological relevance of this missense genetic change resulting in the K87E amino acid switch in MMP8 and its particular role in tumorigenesis. The type of amino acid at position 87, i.e., lysine or glutamic acid, significantly affects the function of MMP8 and its role in the invasion, metastasis, and ultimately clinicopathological outcomes of human cancers.

Although the genetic patterns were studied here and shown to be associated with specific clinicopathological outcomes of papillary thyroid cancer, they are expected to also apply to other types of thyroid tumors and can therefore be diagnostically and prognostically used in these tumors, such as follicular thyroid cancer, Hurthle cell thyroid cancer, poorly differentiated thyroid cancer, anaplastic thyroid cancer, medullary thyroid cancer, and benign thyroid tumors and thyroid nodules. Moreover, as these genetic patterns reflect germline genetic variants, these MMP8 markers commonly exist in the general human population. Thus these markers also predict certain clinicopatholgoical outcomes of other human cancers and can therefore be similarly used to guide their diagnosis, prognostication and appropriate management.

Examples of cancers which can be subjected to similar analyses and predictions based on these same markers include without limitation lung cancer, breast cancer, stomach cancer, pancreatic cancer, liver cancer, colon cancer, ovarian cancer, endometrial cancer, cervical cancer, prostate cancer, kidney cancer, bladder cancer, testicular cancer, bone cancer, brain cancer, head and neck cancer, leukemia, lymphoma, and melanoma. Other skin cancers, such as squamous cell carcinoma and basal cell carcinoma, may also be used. Other blood cancers including lymphomas may also be used.

Additionally, patients who have benign tumors or precancerous lesions, such as thyroid nodules can also be the subject of the genotype determination. The results of the genotype, similar to the case of cancers in patients, may be used to indicate which tumors or lesions are most likely to progress and which are least likely to progress, for example. Thus the genotype of a patient's germline interacts with a patient's tumor to modify its natural history. A prognosis for such patients can be similarly assigned as with cancerous tumors. Non-limiting examples of precancerous lesions are thyroid nodules which may develop into thyroid cancer, nevi which may develop into melanomas, breast adenoma which may develop into breast cancer, and colon polyps which may develop into colon cancer.

Assigning a prognosis is a positive act of sorting a patient into a group to which a particular prognosis has been associated. The assignment requires recording a result, such as in a communiqué or medical record, communicating the result, e.g., to the patient or to a medical professional or family member, or acting on the prognosis, e.g., making a treatment or management decision or performing a treatment or management act based on the prognosis. Other means may be used.

Patients may be assigned to a group of similar patients based on the genotype determined. The group may be involved in a clinical study. The group may be used analytically to process the results of patients receiving similar treatments. The group may be assigned different treatments based on the genotype.

The MMP8 genetic variant markers can be used in combination with other molecular markers to synergistically enhance the diagnostic, prognostic, and therapeutic value in the management of thyroid cancers and other human cancers. These other molecular markers can be mutations, genetic amplifications, genetic copy gain or loss/deletion, genetic rearrangements, epigenetic alterations (e.g., hypermethylation, hypomethylation, histone acetylation, histone methylation, and other types of histone modifications, and expression changes in various microRNA markers), microsatellite instability, loss of heterozygosity, abnormal protein expression patterns, and other molecular changes. Examples of genes, transcripts, and proteins which may be effected include without limitation RET-PTC (e.g., isoforms 1, 2, 3 and other forms), PPARγ/Pax8, RET, H-Ras, K-Ras, N-Ras, k-Raf, B-Raf (BRAF), C-Raf, MEK1/2, ERK1/2, PIK3CA, PIK3CB, PIK3CD, other types of PI3K, PDK, PTEN, Akt-1, Akt-2, Akt-3, mTOR, RASSFIA, RASAL1, ALK, EML4-ALK, other ALK-involving rearrangements, telomerase (and telomeres), beta-catenin, galectin 1 and 3, EGFR, PDGFR alpha and beta, VEGFR-1 and 2, c-MET, KIT, thyroxine receptor beta and alpha, TSHR, TPO, NIS, TTF-1, TTF-2, PAX8, SLC26A4 (pendrin), thyroglobulin, MLH1, MLH3, MSH2, MSH6, PMS1, PMS2, the family of matrix metalloproteinases (including MMP1-23 other than MMP8), PSA, CA-125, CA-19, CEA, calcitonin, NF-kappaB, retinoic acid receptors (e.g., RARbeta2), TIMP3, SLC5A8DAPK, estrogen receptors, STAT3, HMGI, JNK, DUSP26, APC, MSH42, MSH6, TP53, LKB1, STK11, SMAD4, DPC4, ERBB2 (HER2/neu), ETV6, NTRK3, BRCA1, BRCA2, CDKN2, CDK4, TMPRSS2-EGR, Tp16 (p16/INK4/CDKN2), PRCC/TFE3, PSF/TFE3, ASPL/TFE3, CLTC/TFE3, NONO/TFE3, ALPHA/TFEB, FKHR, menin, TGFBR1, E-cadherin, TGF-beta, hypoxia-inducible factor-1alpha, chemokines CXCL1 and CXCL10, MST1, FoxO3, Mst1, urokinase plasminogen activator receptor, thrombospondin-1, neurotrophic tyrosine kinase receptor 1 (NTRK1), GDNF-family receptor-alpha, hepatocyte growth factor, CDH1, and other genes. Markers known to be particularly important in thyroid cancers include miRNA markers, such as upregulation of miR-146b, miR-221, miR-222, miR-155, miR-31 and downregulation of miR-1, miR-34b, miR-130b, and miR-138 in aggressive compared with nonaggressive PTC. Another marker associated with aggressive behavior is mutated BRAF(V600E). Another marker associated with aggressive behavior is IQGAP1 copy number (CN) gain≥3. Combinations of any such markers may be used.

A genotype can be determined using any techniques known in the art. Genomic DNA, cDNA, mRNA, or protein can be analyzed to determine the genotype. Any technique which provides information on the identity of the nucleotide at position 259 of the mRNA or position 87 of the protein can be used. In order to determine the Natick genotype, one must be able to detect both versions of the SNP, if present. Techniques which may be used include without limitation, RT-PCR, PCR, nucleotide sequencing, ELISA, immunohistochemistry, immunoprecipitation, allele specific amplification, allele specific ligation, hybridization to allele specific probes, immunoelectrophoresis, etc.

A test sample from the patient need not be from a tumor. The SNP occurs in all cells of the body, so any sample that is convenient may be used. Blood is an obvious choice because of ease of harvesting.

We examined the MMP8, AKT5 and PIK3R1 genes for their mutation status in various thyroid cancers and GNAQ in anaplastic thyroid cancer and found no mutation in them. A positive finding in the present study is the discovery for the first time a G735S EGFR mutation in thyroid cancer although it is an infrequent event. This mutation was first identified in lung cancer and subsequently in prostate cancer (18, 19). The G735 residue is located on the beta-strand of the N-terminal lobe. Three-D rendering of the tyrosine kinase domain has suggested that a possible mechanism for EGER deregulation by the G735S mutation is a conformational change of the kinase domain, leading to its activation (19). Functional analyses demonstrated that the G735S EGFR mutant was a gain-of-function mutation with increased tyrosine kinase activity associated with increased signaling activities of the STAT, MAPK and PI3K/AKT pathways, as reflected by the phosphorylation of STAT, AKT and ERK as well as increased cell proliferation, anchorage-independent colony formation and invasion (20). EGFR mutations of other types have been also reported in PTC of Greek (15) and Japanese patients (9) and no mutation of this gene was found in FTC and ATC of American patients (4). The prevalence of the EGER mutation in the PTC patients in the present study was 5% (1/21), same to the prevalence (5%, 2/43) of EGER mutations in Greek PTC patients (15), but lower than that (30%, 7/23) in Japanese PTC patients (9). Different ethnic backgrounds may explain this variation in prevalence. It is likely that PTC patients harboring mutations in the EGER gene may respond to therapeutic targeting using specific EGFR inhibitors or dually targeting the PI3K/AKT and MAPK pathways using MEK and AKT inhibitors.

Somatic mutations in MMP8 and PIK3R1 have not been investigated previously in thyroid cancer. Akt3 has not been analyzed in follicular and anaplastic thyroid cancer and GNAQ has not been analyzed in anaplastic thyroid cancer. Our mutational analyses in the present study showed absence of somatic mutations in these genes in thyroid cancer. These findings suggest that genetic alterations in these genes may not play a significant role in the tumorigenesis of this cancer. It is probably not surprising that GNAQ, MMP8, Akt3 and PIK3R1 gene mutations are not common in thyroid cancer since many of the upstream effectors such as EGFR, RET/PTC, RAS, BRAF, PTEN, PIK3CA, PIK3CB and PDK1 are commonly activated via mutations or genetic amplifications that can independently activate the MAPK or the PI3K/AKT pathway in thyroid cancers (4). For example the BRAE V600E mutation is very common in thyroid cancers such as papillary thyroid cancers. Moreover, unlike Akt1 and Akt2, Akt3 may not play a significant role in the tumorigenesis of thyroid cancer (21, 22). Therefore, genetic alterations in the Akt3 gene might predictably unnecessary for thyroid cancer tumorigenesis.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods
Cell Lines, Tumor Samples, and DNA Extraction

The thyroid cancer cell lines (K1, K5, OCU717-1, FB-1, SW1736, BCPAP, HTh117, HTh74, KAT 18, FTC133 and C643) and thyroid tumor, melanoma and colon cancer samples used were as described previously with local Institutional Review Board (IRB) approval (116). Cell lines were cultured in RPMI-1640 medium supplemented with 10% fetal bovine serum (FBS), streptomycin (100 μg/mL), penicillin (100 units/mL) and 2 mM glutamine. Genomic DNA from cell lines and tumors was isolated by standard phenol-chloroform extraction and ethanol precipitation procedures (16).

PCR Amplification and Sequencing of GNAQ, MMP8, AKT3, EGFR and PIK3R1 Genes

The primer sequences and PCR conditions for the amplification of exon 5 of the GNAQ gene, exon 2 of the MMP8 gene, and exons 18, 19 and 21 of the EGER gene are as described previously (5, 6, 17). The primer sequences for the amplification of exon 2 and exon 12 of the AKT3 gene are as follows: (exon 2) AKT3-2F 5'-TGGAGGCCAGTGTTG-TAGGAC-3'(SEQ ID NO: 1); AKT3-2R 5'-ATAGCCTAA-GATATCTGACAC-3' (SEQ ID NO: 2), (exon 12) AKT3-12F 5'-AGCGACTCAGCATTGTAGACT-3'(SEQ ID NO: 3); AKT3-12R 5'-TCACTGTGGAATTTGATCTTG-3'(SEQ ID NO: 4). PCR reaction conditions were as follows, after initial denaturation, at 94° C. for 2 min, amplification was performed at 94° C. for 1 min, 60° C. for 1 min for 35 cycles with final extension at 72° C. for 7 min and the same PCR conditions were followed for the amplification of exon 12 of AKT3 except for the annealing temperature at 58° C. The primers sequences PIK3R1-14F 5'-AAACTGCTGGGAAACCAT-AGT-3'(SEQ ID NO: 5), PIK3R1-14R 5'-TAACTCATCCT-GAATTGTAGC-3'(SEQ ID NO: 6), PIK3R1-16F 5'-AAGA-CAGCAAGGCAGGCTGAT-3'(SEQ ID NO: 7), PIK3R1-16R 5'-CTATGTCAAATCTTTGCCCCC-3'(SEQ ID NO: 8), PIK3R1-17F 5'-TGAGACTGCACAATAATGCTT-3' (SEQ ID NO: 9) and PIK3R1-17R 5'-CTCAATTCACAGAT-CAGACTG-3' (SEQ ID NO: 10) were used for the PCR amplification of exon 14, 16 and 17 respectively. Annealing temperature was 57° C. for exon 14 and 17 and 60° C. for exon 16. The PCR products were directly sequenced using a Big Dye terminator v3.1 cycle sequencing ready reaction kit (Applied Biosystems). These exons were examined because they harbored most of the reported mutations in these genes. Gene Bank accession numbers are NM_002072.2 (GATAQ), NM_002424.2 (MMP8), NM_ NM 005465.3 (AKT3), NM_005228.3 (EGFR) and NM_181523.1 (PIK3R1).

Example 2

We examined exon 5 of the GNAQ gene for mutations in the present study since all of the known GATAQ mutations have been reported in codon 209 in this exon. Exon 2 of the MMP8 gene and exons 18, 19 and 21 of the EGFR gene were selected for sequencing as they have recently been shown to carry somatic mutations in other human cancers. Exons 2 and 12 of AKT3 were similarly chosen for analysis for their carrying mutations in other cancers. Exons 14, 16 and 17 of the PIK3R1 gene were selected for analysis also because they were the most mutated exons in PIK3R1.

Our sequencing results showed no mutation in and around the hot spot codon 209 in the GNAQ gene in 12 thyroid cancer cell lines and 40 thyroid cancer samples (including 20 FTC and 20 ATC). We did not examine PTC as this cancer was found to harbor no GNAQ mutation previously (11). The normal amino acid, glutamine, encoded by codon 209 of the GNAQ gene lies within the RAS-like domain of GNAQ (corresponding to residue 61 of Ras) and is essential for GTP hydrolysis. In members of RAS family, mutations at this site and at codon 12 cause loss of GTPase activity with constitutive activation of Ras. Given this similarity of GNAQ$^{Q209L}$ mutation with Ras mutations and the fact that melanoma and colon cancer are similar to thyroid cancer in terms of their high prevalence of Ras mutations, we additionally analyzed 20 cutaneous melanoma and 20 colon cancer samples for the GNAQ mutation and found that none of them harbored this mutation.

Figure 1A:
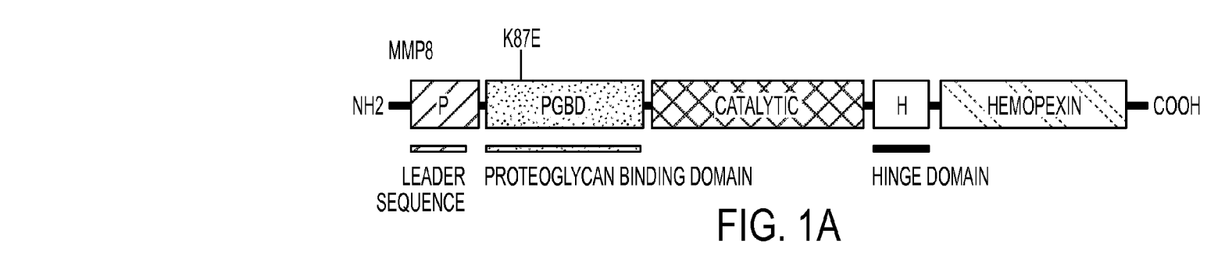
(FIG. 1A) Schematic diagram of domains of MMP8 protein showing a single nucleotide polymorphism (K87E) identified in thyroid cancer. The MMP8 gene is located on chromosome 11q22.3 contains 10 exons and intervening sequences.
Figure 1B:
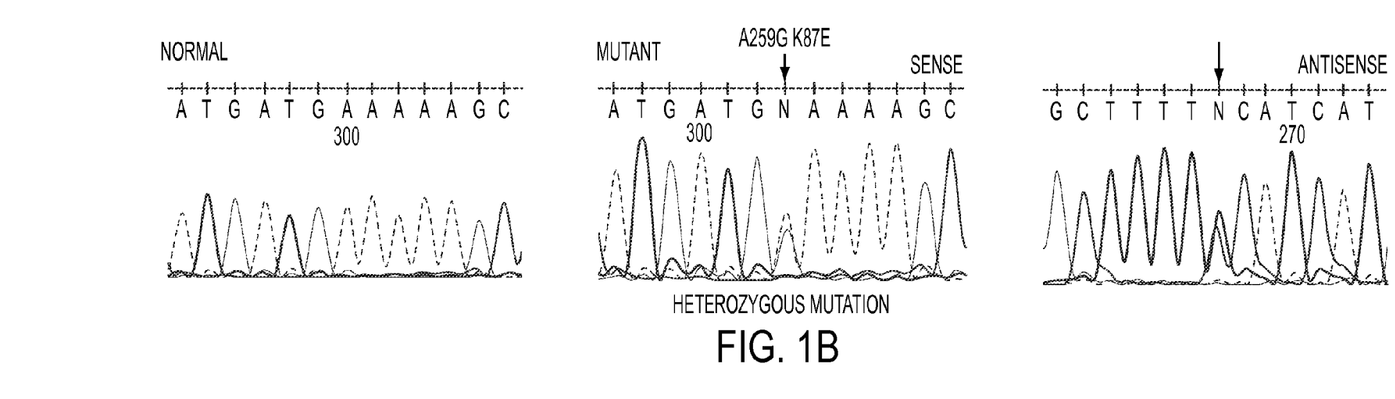
(FIG. 1B The sequencing results were shown with a representative sense and antisense sequence profile of a single nucleotide polymorphisms (A259G) found in exon 2 of MMP8 gene.
Figure 1C:
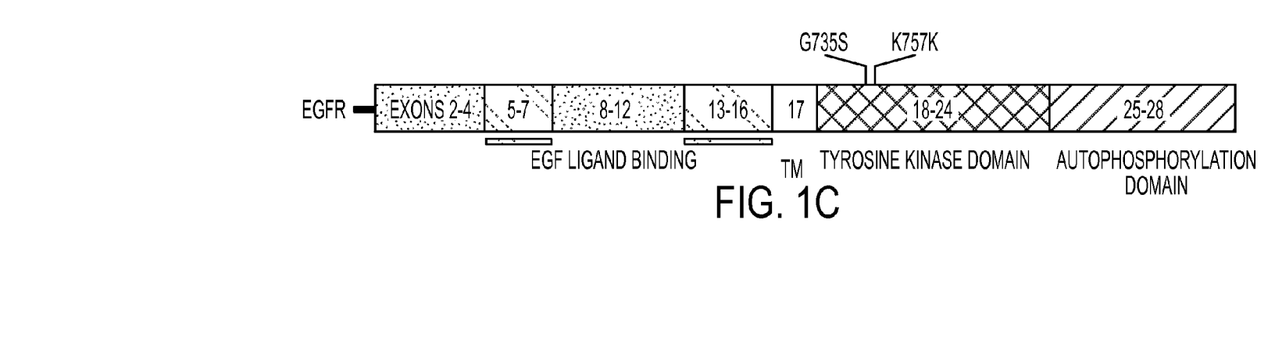
Figure 1D:
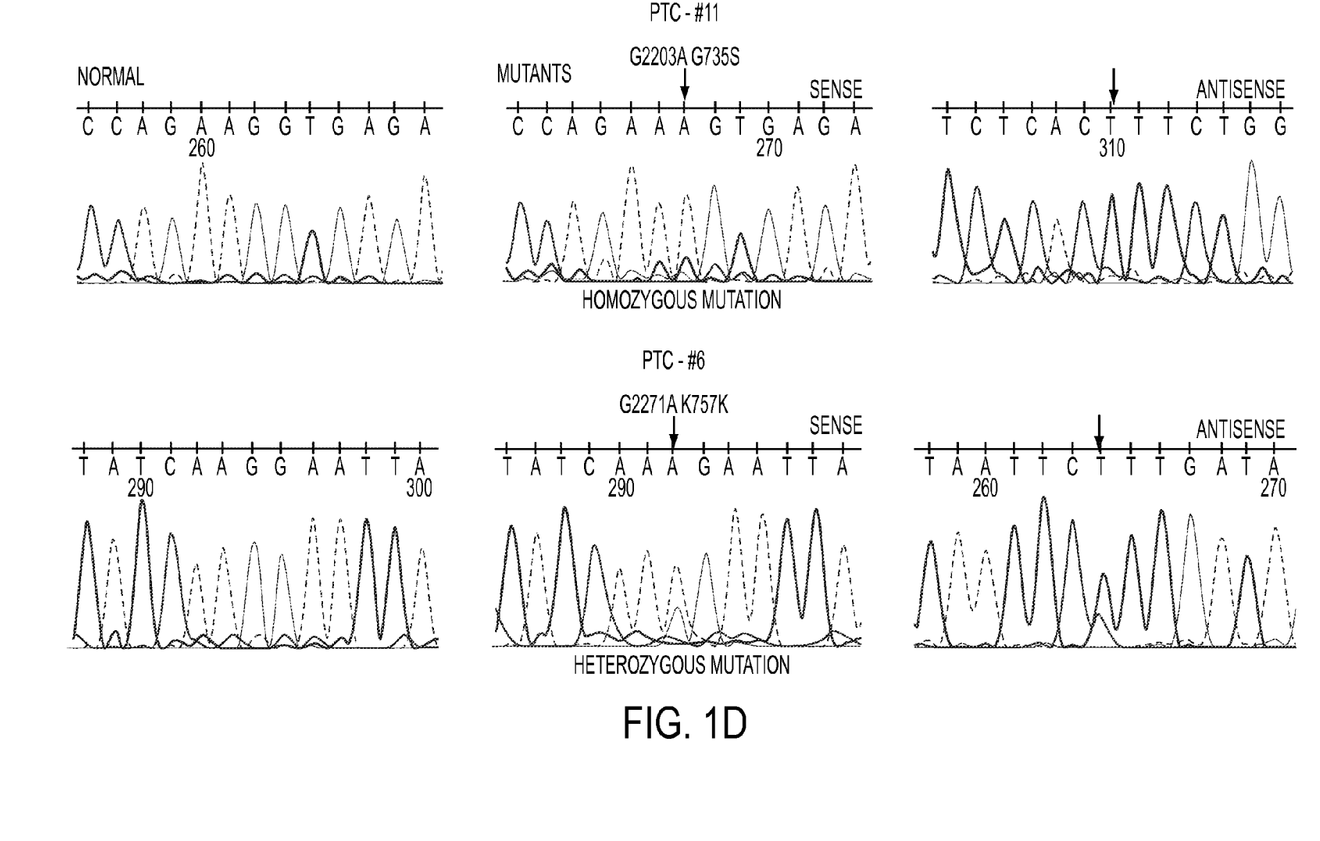
(FIG. 1D) The sequencing results were shown with sense and antisense sequence profiles of a mutation (G2203A) and a single nucleotide polymorphism (G2271A) found in exon 19 of EGFR gene. Arrow indicates mutated nucleotide. The nucleotide and amino acid alterations are indicated above the arrow. Nucleotide numbers refers to the position within coding sequence, where position 1 corresponds to the first position of the initiation codon. All the samples were sequenced in two repeated examinations with independent PCR by forward and reverse primers.

We did not find any novel MMP8 mutation in 12 thyroid cancer cell lines and 31 PTC, 20 FTC and 20 ATC tumor samples. As illustrated in FIG. 1, we observed a frequent homozygous/heterozygous A>G transition at nucleotide position 259, resulting in codon 87 switch between AAA and GAA and amino acid 87 switch between lysine and glutamic acid (K87E) in exon 2 of MMP8. This represents a single nucleotide polymorphism (SNP) (rs1940475) reported in the SNP data base (http://www.ncbi.nlm.nih.gov/projects/SNP/).

We found the G259 pattern in 25 of 31 (80.6%) PTC, 14 of 19 (73.6%) FTC and 8 of 9 (88.8%) ATC. Conversely, the A259 pattern was found in 19.4%, 26.4%, and 11.2% of these tumors, respectively.

We did not find any AKT3 mutation in 12 thyroid cancer cell lines and 20 PTC, 20 FTC and 20 ATC tumor samples. We also did not find any PIK3R1 mutation in 12 thyroid cancer cell lines and 20 PTC, 32 FTC and 32 ATC samples.

However, we found an EGFR mutation in 1 of 21 (5%) PTC tumor samples. This mutation was not found in 12 thyroid cancer cell lines. As illustrated in FIG. 1, this mutation is a homozygous missense mutation resulting in G>A transition at nucleotide position 2203 of the EGFR gene. This mutation caused codon 735 to change from GGT>AGT, resulting in the amino acid change G735S in the EGFR protein. We also found a rare and novel silent mutation resulting in G>A transition at the nucleotide position 2271 and it has not been reported in the SNP data base (FIG. 1). FIG. 1 shows the mutations and SNP identified and their related protein domain.

Example 3

We performed 3-way and 2-way analyses to determine if there was an association between gat nucleotide 259 in codon 87 of the MMP8 gene with poor clinicopathological outcomes in cancer. Results in tables 1-3 show that the genotype AA at nucleotide position 259 in codon 87 of the MMP8 gene is most significantly associated with several poor clinicopathiogical outcomes of papillary thyroid cancer, including extrathyroidal invasion, vascular invasion, cancer recurrence/persistence, distant metastasis, advanced tumor stages. Most importantly, AA is strongly associated with disease recurrence of thyroid cancer. The genotype GG is to some extent associated with some of these clinicopathological characteristics. The genotype AG is least associated with these tumor characteristics. Therefore, genotype AA is associated with a poorer prognosis of thyroid cancer, genotype AG is associated with a better prognosis, and genotype GG is associated with an intermediate prognosis of thyroid cancer. This genotypic information is expected to be useful in guiding the prognostication and in selecting an appropriate treatment of thyroid and other cancers. It should be noted that the genotypes AA, GG, and AG termed here would be TT, CC, and TC if the complementary (non-coding) DNA strand is used for orientation.

TABLE 1

Association of Genotypes at Nucleotide 259 in Codon 87 of the MMP8 Gene with Poor Clinicopathological Outcomes of Papillary Thyroid Cancer (3-way and 2-way analyses)

| Clinicopathological Variable | Genotype | Yes | P | Genotype | Yes | P | REMARKS |
|---|---|---|---|---|---|---|---|
| Age (years) | AA | 47.9 ± 14.2 | 0.15 | AA | 47.9 ± 14.1 | 0.063 | P = 0.11 |
|  | AG | 45.0 ± 13.3 |  | AG/GG | 44.7 ± 13.8 |  | by Mann |
|  | GG | 44.1 ± 14.7 |  |  |  |  | Whitney |
| Tumor Size (cm) | AA | 2.2 ± 1.4 | 0.24 | AA | 2.2 ± 1.4 | 0.89 | P = 0.95 |
|  | AG | 2.0 ± 1.4 |  | AG/GG | 2.1 ± 1.5 |  | by Mann |
|  | GG | 2.3 ± 1.6 |  |  |  |  | Whitney |
| Male gender | AA | 26 (30.6) | 0.86 | AA | 26/85 (30.6) | 0.69 |  |
|  | AG | 54 (27.4) |  | AG/GG | 86/311 (27.7) |  |  |
|  | GG | 32 (28.1) |  |  |  |  |  |
| Extrathyroidal Invasion | AA | 25/84 (29.8) | 0.001 | AA | 25/84 (29.8) | 0.005 |  |
|  | AG | 23/196 (11.7) |  | AG/GG | 48/310 (15.5) |  |  |
|  | GG | 25/114 (21.9) |  |  |  |  |  |
| Vascular invasion | AA | 26/83 (31.3) | 0.005 | AA | 26/83 (31.3) | 0.007 |  |
|  | AG | 28/193 (14.5) |  | AG/GG | 52/304 (17.1) |  |  |
|  | GG | 24/111 (21.6) |  |  |  |  |  |
| Tumor Multifocality | AA | 37/85 (43.5) | 0.095 | AA | 37/85 (43.5) | 0.63 |  |
|  | AG | 100/196 (51.0) |  | AG/GG | 144/310 (46.5) |  |  |
|  | GG | 44/114 (38.6) |  |  |  |  |  |
| Lymph node metastases | AA | 26/85 (30.6) | 0.77 | AA | 26/85 (30.6) | 0.78 |  |
|  | AG | 66/197 (33.6) |  | AG/GG | 100/311 (32.2) |  |  |
|  | GG | 34/114 (29.8) |  |  |  |  |  |
| Tumor Persistence/Recurrence | AA | 20/78 (25.6) | 0.038 | AA | 20/78 (25.6) | 0.027 |  |
|  | AG | 25/194 (12.9) |  | AG/GG | 44/306 (14.4) |  |  |
|  | GG | 19/112 (17.0) |  |  |  |  |  |

TABLE 1-continued

Association of Genotypes at Nucleotide 259 in Codon 87 of the
MMP8 Gene with Poor Clinicopathological Outcomes of Papillary Thyroid
Cancer (3-way and 2-way analyses)

| Clinicopathological Variable | Genotype | Yes | P | Genotype | Yes | P | REMARKS |
|---|---|---|---|---|---|---|---|
| Distant Metastases | AA | 7/84 (8.3) | 0.16 | AA | 7/84 (8.3) | 0.16 | |
| | AG | 6/197 (3.0) | | AG/GG | 12/311 (3.9) | | |
| | GG | 6/114 (5.3) | | | | | |
| Death | AA | 0/83 (0) | 0.12 | AA | 0/83 (0) | 0.67 | |
| | AG | 1/196 (0.5) | | AG/GG | 4/310 (1.3) | | |
| | GG | 3/114 (2.6) | | | | | |
| Stage III & IV | AA | 16/85 (18.8) | 0.74 | AA | 16/85 (18.8) | 0.98 | |
| | AG | 36/196 (18.4) | | AG/GG | 61/310 (19.7) | | |
| | GG | 25/114 (21.9) | | | | | |
| Tumor stage 3 & 4 | AA | 20/85 (23.5) | 0.125 | AA | 20/85 (23.5) | 0.17 | |
| | AG | 27/192 (14.1) | | AG/GG | 50/306 (16.3) | | |
| | GG | 23/114 (20.2) | | | | | |

TABLE 2

Comparison of Genotype AA vs. AG and AA vs. GG at Position 259 of the MMP8 Gene for Association
with Clinicopathological Outcomes of Papillary Thyroid Cancer

| Clinicopathological Variable | Genotype | Yes | P | Genotype | Yes | P |
|---|---|---|---|---|---|---|
| Age (years) | AA | 47.9 ± 14.1 | 0.11 | AA | 47.9 ± 14.1 | 0.07 |
| | AG | 45.0 ± 13.3 | | GG | 44.1 ± 14.7 | |
| Tumor Size (cm) | AA | 2.2 ± 1.4 | 0.47 | AA | 2.2 ± 1.4 | 0.47 |
| | AG | 2.0 ± 1.4 | | GG | 2.3 ± 1.6 | |
| Male gender | AA | 26/85 (30.6) | 0.69 | AA | 26/85 (30.6) | 0.82 |
| | AG | 54/197 (27.4) | | GG | 32/114 (28.1) | |
| Extrathyroidal Invasion | AA | 25/84 (29.8) | 0.000 | AA | 25/84 (29.8) | 0.28 |
| | AG | 23/196 (11.7) | | GG | 25/114 (21.9) | |
| Vascular invasion | AA | 26/83 (31.3) | 0.002 | AA | 26/83 (31.3) | 0.17 |
| | AG | 28/193 (14.5) | | GG | 24/111 (21.6) | |
| Tumor Multifocality | AA | 37/85 (43.5) | 0.31 | AA | 37/85 (43.5) | 0.58 |
| | AG | 100/196 (51.0) | | GG | 44/114 (38.6) | |
| Lymph node metastases | AA | 26/85 (30.6) | 0.73 | AA | 26/85 (30.6) | 1.00 |
| | AG | 66/197 (33.5) | | GG | 34/114 (29.8) | |
| Tumor Persistence/Recurrence | AA | 20/78 (25.6) | 0.017 | AA | 20/78 (25.6) | 0.20 |
| | AG | 25/194 (12.9) | | GG | 19/112 (17.0) | |
| Distant Metastases | AA | 7/84 (8.3) | 0.11 | AA | 7/84 (8.3) | 0.57 |
| | AG | 6/197 (3.0) | | GG | 6/114 (5.3) | |
| Death | AA | 0/83 (0) | 1.00 | AA | 0/83 (0) | 0.37 |
| | AG | 1/196 (0.5) | | GG | 3/114 (2.6) | |
| Stage III & IV | AA | 16/85 (18.8) | 1.00 | AA | 16/85 (18.8) | 0.77 |
| | AG | 36/196 (18.4) | | GG | 25/114 (21.9) | |
| Tumor stage III & IV | AA | 20/85 (23.5) | 0.078 | AA | 20/85 (23.5) | 0.69 |
| | AG | 27/192 (14.1) | | GG | 23/114 (20.2) | |

TABLE 3

Comparison of AG with GG at Position 259 of the MMP8 Gene

| Clinicopathological Variable | Genotype | Yes | P |
|---|---|---|---|
| Age (years) | AG | 45.0 ± 13.3 | 0.58 |
| | GG | 44.1 ± 14.7 | |
| Tumor Size (cm) | AG | 2.0 ± 1.4 | 0.10 |
| | GG | 2.3 ± 1.6 | |
| Male gender | AG | 54/197 (27.4) | 1.00 |
| | GG | 32/114 (28.1) | |
| Extrathyroidal Invasion | AG | 23/196 (11.7) | 0.026 |
| | GG | 25/114 (21.9) | |
| Vascular invasion | AG | 28/193 (14.5) | 0.15 |
| | GG | 24/111 (21.6) | |
| Lymph node metastases | AG | 66/197 (33.5) | 0.59 |
| | GG | 34/114 (29.8) | |
| Tumor Persistence/Recurrence | AG | 25/194 (12.9) | 0.42 |
| | GG | 19/112 (17.0) | |
| Distant Metastases | AG | 6/197 (3.0) | 0.50 |
| | GG | 6/114 (5.3) | |
| Death | AG | 1/196 (0.5) | 0.28 |
| | GG | 3/114 (2.6) | |
| Stage III & IV | AG | 36/196 (18.4) | 0.54 |
| | GG | 25/114 (21.9) | |
| Tumor stage III & IV | AG | 27/192 (14.1) | 0.22 |
| | GG | 23/114 (20.2) | |

REFERENCES

The disclosure of each reference cited is expressly incorporated herein.
1. Leenhardt L, Cirosclaude P & Cherie-Challine L. Increased incidence of thyroid carcinoma in France: a true epdemic or thyroid nodule management effects? Report from the French Thyroid Cancer Committee. Thyroid 14:10561060, 2004.
2. Sprague B L, Warren Andersen S &. Trentham-Dietz A. Thyroid cancer incidence and socioeconomic indicators of health care access. Cancer Causes and Control 19:585-593, 2008.
3. Hundahl, I. D. Fleming, A. M. Fremgen and Menck, A national cancer data base report on 53,856 cases of thyroid carcinoma treated in the U.S., 1985-1995. Cancer 83:2638-2648, 1998.
4. Liu Z, Hou P, Ji M, Guan H, Studeman K, Jensen K, et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab 93:3106-3116, 2008.
5. Van Raamsdonk C D, Bezrookove V, Green G, Bauer J, Gaugler L, O'Brien J M, et al. Frequent somatic mutations of GNAQ in uveal melanoma and bluenaevi. Nature 457: 599-602, 2009.
6. Palavalli L H, Prickett T D, Wunderlich J R, Wei X, Burrell A S, Porter-Gill P, et al. Analysis of the matrix metalloproteinase family reveals that MMP8 is often mutated in melanoma. Nat Genet 41:518-520, 2009.
7. Davies M A, Sternke-Hale K, Tellez C. Calderone T L, Deng W, Prieto V G, et al. A novel AKT3 mutation in melanoma tumors and cell lines. Br J Cancer 99:1265-1268, 2008.
8. Dutt A, Salvesen H B, Greulich H, Sellers W R, Beroukhim R & Meyerson M. Somatic mutations are present in all members of the AKT family in endometrial carcinoma. Br J Cancer 101:1218-1219, 2009.
9. Masago K, Asato R, Fujita S, Hirano S, Tamura Y, Kanda T, et al., Epidermal growth factor receptor mutations in papillary thyroid carcinoma. Int J Cancer 124:2744-2749, 2009.
10. Jaiswal B S, Janakiraman V, Kljavin N M, Chaudhuri S, Stem H M, Wang W, et al. Somatic mutations in p85a promote tumorigenesis through class IA PI3K activation. Cancer Cell 16:463-474, 2009.
11. Matsuse M, Mitsutake N, Nishihara E, Rogounovitch T, Saenko V, Rumyantsev P, et al, Lack of GNAQ hotpot mutation in papillary thyroid carcinomas. Thyroid 19: 921-922, 2009.
12. Lamba 5, Felicioni L, Buttitta. F, Bleeker F E, Malatesta S, Corbo V, et al. Mutational profile of GNAQQ209 in human tumors. PLoS One 4:e6833, 2009.
13. Cassol C A, Guo M, Ezzat 5, Asa S L. GNAq mutations are not identified in papillary thyroid carcinomas and hyperfunctioning thyroid nodules. Endocr Pathol 21:250-2, 2010.
14. Sozopoulos E, Litsiou, Voutsinas G, Mitsiades N, Anagnostakis N, Tseva T, et al. Mutational and immunohistochemical study of the PI3K/Akt pathway in papillary thyroid carcinoma in Greece. Endocr Pathol 21:90-100, 2010.
15. Mitsiades C S, Kotoula V, Poulaki V, Sozopoulos E, Negri J, Charalambous E, et al. Epidermal growth factor receptor as a therapeutic target in human thyroid carcinoma: mutational and functional analysis. J Clin Endocrinol Metab 91:3662-3666, 2006.
16. Murugan A K, Dong J, Xie J & Xing M. MEK1 mutations, but not ERK2 mutations, occur in melanomas and colon carcinomas, but none in thyroid carcinomas. Cell Cycle 8:2122-2124, 2009.
17, Nagai Y, Miyazawa Huqun, Tanaka T, Udagawa K, Kato 141, et al. Genetic heterogeneity of the epidermal growth factor receptor in non-small cell lung cancer cell lines revealed by a rapid and sensitive detection system, the peptide nucleic acid-locked nucleic acid PCR clamp. Cancer Res 65:7276-7282, 2005.
18. Tsao M A, Sakurada A, Cutz J C, Zhu C Q, Kamel-Reid S, Squire J, et al. Erlotinib in lung cancer—molecular and clinical predictors of outcome. N Engl J Med 353:133-144, 2005.
19. Douglas D A, Zhong H, Ro J Y, Oddoux C, Berger A D, Pincus M R, et al. Novel mutations of epidermal growth factor receptor in localized prostate cancer. Front Biosci 11:2518-2525, 2006.
20, Cai C Q, Peng Y. Buckley M T, Wei J, Chen F, Liebes L, et al. Epidermal growth factor receptor activation in prostate cancer by three novel missense mutations. Oncogene 27:3201-3210, 2008.
21, Ringel M D, Hayre N. Saito J, Saunier B, Schuppert F, Burch H, et al. Overexpression and overactivation of Akt in thyroid carcinoma. Cancer Res 6:6105-6111, 2001.
22. Ricarte-Filho J C, Ryder M, Chitale D A, Rivera M, Heguy A, Ladanyi M, et al. Mutational profile of advanced primary and metastatic radioactive iodine-refractory thyroid cancers reveals distinct pathogenetic roles for BRAF, PIK3CA, and AKT1. Cancer Res 69:4885-93, 2009.

The invention claimed is:

1. A method for predicting recurrence of thyroid cancer in a human patient comprising the steps of:
   a. PCR amplifying exon 2 of the matrix metalloproteinase 8 (MMP8) gene from a genomic DNA sample obtained from the subject using primers that will amplify the nucleic acid sequence at rs1940475;
   b. sequencing the amplified PCR products to identify the genotype at rs1940475; and
   c. predicting (i) an increased risk of tumor recurrence in the subject if the AA genotype is detected; (ii) a decreased risk of tumor recurrence in the subject if the AG genotype is detected; or (iii) an intermediate risk of tumor recurrence in the subject if the GG genotype is detected.

* * * * *